United States Patent
Shan et al.

(10) Patent No.: US 12,165,775 B1
(45) Date of Patent: Dec. 10, 2024

(54) COMMUNICATIONS CENTRIC MANAGEMENT PLATFORM

(71) Applicant: Verily Life Sciences LLC, Mountain View, CA (US)

(72) Inventors: Peilun Shan, San Francisco, CA (US); Aaron Stoertz, Redwood City, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

(21) Appl. No.: 18/184,601

(22) Filed: Mar. 15, 2023

Related U.S. Application Data

(63) Continuation of application No. 16/865,136, filed on May 1, 2020, now Pat. No. 11,636,955.

(Continued)

(51) Int. Cl.

| | | |
|---|---|---|
| *G16H 80/00* | (2018.01) | |
| *G06F 21/62* | (2013.01) | |
| *G06N 20/00* | (2019.01) | |
| *G06Q 50/26* | (2024.01) | |
| *G16H 10/60* | (2018.01) | |
| *G16H 40/20* | (2018.01) | |

(Continued)

(52) U.S. Cl.
CPC ......... *G16H 80/00* (2018.01); *G06F 21/6245* (2013.01); *G06N 20/00* (2019.01); *G16H 10/60* (2018.01); *G16H 40/20* (2018.01); *G16H 50/70* (2018.01); *H04L 67/12* (2013.01); *G06Q 50/265* (2013.01)

(58) Field of Classification Search
CPC ........ G16H 80/00; G16H 50/70; G16H 40/20; G16H 10/60; H04L 67/12; G06Q 50/265; G06N 20/00; G06F 21/6245
See application file for complete search history.

(56) References Cited

U.S. PATENT DOCUMENTS

| | | |
|---|---|---|
| 9,507,486 B1 | 11/2016 | Reed et al. |
| 9,953,181 B2 | 4/2018 | Dunaway |

(Continued)

FOREIGN PATENT DOCUMENTS

| | | |
|---|---|---|
| WO | 2001080092 | 10/2001 |

OTHER PUBLICATIONS

Jeong et al., Development of Patient Status-Based Dynamic Access System for Medical Information Systems, 7 Symmetry 1028-1039 (Jun. 8, 2015) (Year: 2015).*

(Continued)

*Primary Examiner* — Jordan L Jackson
(74) *Attorney, Agent, or Firm* — Perkins Coie LLP

(57) ABSTRACT

The disclosed embodiments include a computer-implemented method for communications centric care. A caregiver interface serves a patient interface in accordance with a disease management program to collaboratively lead the patient to recover from a disease. The method can include obtaining content items relating to a patient and labeling each content item as either a secure content item or an unsecure content item, and then comparing the labels with identifiers of the patient, the caregiver, and/or a schedule of key events of the disease management program. The content items are selectively bifurcated for the patient and/or caregiver interfaces. As such, the interfaces can manage communications in accordance with the disease management program.

19 Claims, 12 Drawing Sheets

Related U.S. Application Data

(60) Provisional application No. 62/841,465, filed on May 1, 2019.

(51) Int. Cl.
*G16H 50/70* (2018.01)
*H04L 67/12* (2022.01)

(56) References Cited

U.S. PATENT DOCUMENTS

| | | |
|---|---|---|
| 10,425,355 B1 | 9/2019 | Manoukian et al. |
| 11,023,112 B2 | 6/2021 | Narayanaswami |
| 2005/0288965 A1 | 12/2005 | Van et al. |
| 2010/0177950 A1 | 7/2010 | Donovan et al. |
| 2010/0179831 A1 | 7/2010 | Brown et al. |
| 2011/0119307 A1 | 5/2011 | Unger et al. |
| 2012/0278095 A1 | 11/2012 | Homchowdhury et al. |
| 2012/0290316 A1 | 11/2012 | Tidhar |
| 2013/0340060 A1 | 12/2013 | Dirico et al. |
| 2015/0254431 A1 | 9/2015 | Gaertner et al. |
| 2015/0356701 A1 | 12/2015 | Gandy et al. |
| 2017/0140109 A1 | 5/2017 | Kheifetz et al. |
| 2017/0199980 A1 | 7/2017 | Erickson |
| 2018/0020001 A1* | 1/2018 | White ............... H04L 63/0428 |
| 2018/0053011 A1 | 2/2018 | East et al. |
| 2019/0080416 A1 | 3/2019 | Smith et al. |
| 2019/0110754 A1 | 4/2019 | Rao et al. |
| 2020/0042845 A1 | 2/2020 | Rasmussen |
| 2020/0279658 A1 | 9/2020 | Rao et al. |

OTHER PUBLICATIONS

Lillian Røstad and Øystein Nytro, Towards Dynamic Access Control for Healthcare Information Systems, 136 Studies in Health Tech and Informatics 703-708 (Feb. 2008) (Year: 2008).*

Marcelo Antonio de Carvalho Junior and Paulo Bandiera-Paiva, Health Information System Role-Based Access Control Current Security Trends and Challenges, J of Healthcare Engineering 1-8 (Feb. 19, 2018) (Year: 2018).*

Kapsalis et al., A dynamic context-aware access control architecture for e-services, 25 Computers & Security 507-521 (Year: 2006).*

Jeong et al., Development of Patient Status-Based Dynamic Access System for Medical Information Systems, 7 Symmetry 1028-1039 (Jun. 8, 2015).

Lillian R0stad and 0ystein Nytro, Towards Dynamic Access Control for Healthcare Information Systems, 136 Studies in Heal TH Tech and Informatics 703-708 (Feb. 2008).

Marcelo Antonio de Carvalho Junior and Paulo Bandiera-Paiva, Health Information System Role-Based Access Control Current Security Trends and Challenges, J of Heal TH Care Engineering 1-8 (Feb. 19, 2018).

Divshali et al., Application of Bifurcation theory in Dynamic Security Constrained Optimal Dispatch in deregulated power system, 93 Electrical Eng 157-166 (Year: 2011), 2011.

Greene et al., Secure sharing of mHealth data streams through cryptographically-enforced access control, 12 Smart Health 49-65 (Available online Apr. 17, 2018) (Year: 2018), 2018.

Rezaeibagha et al., Practical and secure telemedicine systems for user mobility, 78 J of Biomedical Informatics 24-32 (2018) (Year: 2018), 2018.

Benes, Digital Bifurcation Analysis ofTCP Dynamics: TACAS 2019, Part II, LNCS 11428, 339-356 (Apr. 3, 2019) (Year: 2019), 2019.

Website: wwwallscripts.com/market-solutions/hospitals-health-systems; retrieved from the internet on Jul. 1, 2020; 5 pages; 2020.

* cited by examiner

COMMUNICATIONS CENTRIC MANAGEMENT PLATFORM

CROSS-REFERENCE TO RELATED APPLICATION

This application is a continuation of U.S. patent application Ser. No. 16/865,136, filed May 1, 2020, titled "Communications Centric Management Platform," which claims the benefit of U.S. Provisional Patent Application No. 62/841,465, filed May 1, 2019, titled "Communication-Centered Care Management Platform," which is incorporated herein by reference in its entirety.

TECHNICAL FIELD

The disclosed teachings generally relate to a communications architecture. The disclosed teachings more particularly relate to an architecture for communications management of a primary interface for a primary user and a secondary interface for a secondary user, where the secondary user supports the primary user.

BACKGROUND

Disease management is a system of coordinated healthcare interventions and communications for populations with conditions in which patient self-care efforts are significant. Successful disease management requires sharing relevant information in a structured manner among stakeholders. However, stakeholders are people with different perspectives, who have access to different sources of information, and communicate in different ways. For example, a patient's perspective can vastly differ from a familial supporter, which can vastly differ from a professional caretaker. The waves of emotions in a disease management journey can negatively impact how patients care for themselves and how caregivers care for the patients. Further, the information that could aid in disease management is scattered all over the internet or only accessible to some stakeholders. Tracking pieces of information discovered by stakeholders is nearly impossible, and unstructured research and communications can result in redundant information that inundates patients and caregivers, creates daunting expectations, and results in isolation. Moreover, caregivers and patients suffer when they stumble through trial and error to find solutions that work. This is a major drawback in disease management because timely communications of key information between a patient and a caregiver is critical for the patient to complete a disease management journey with a successful outcome. Thus, typical disease management involves unstructured, untimely, and inconsistent communications of unreliable information.

BRIEF DESCRIPTION OF THE DRAWINGS

Various features and attributes of the disclosed technology will become more apparent to those skilled in the art from a study of the Detailed Description in conjunction with the drawings. Embodiments of the disclosed technology are illustrated by way of example and not limitation in the drawings, in which like references indicate similar elements.

Figure 1:
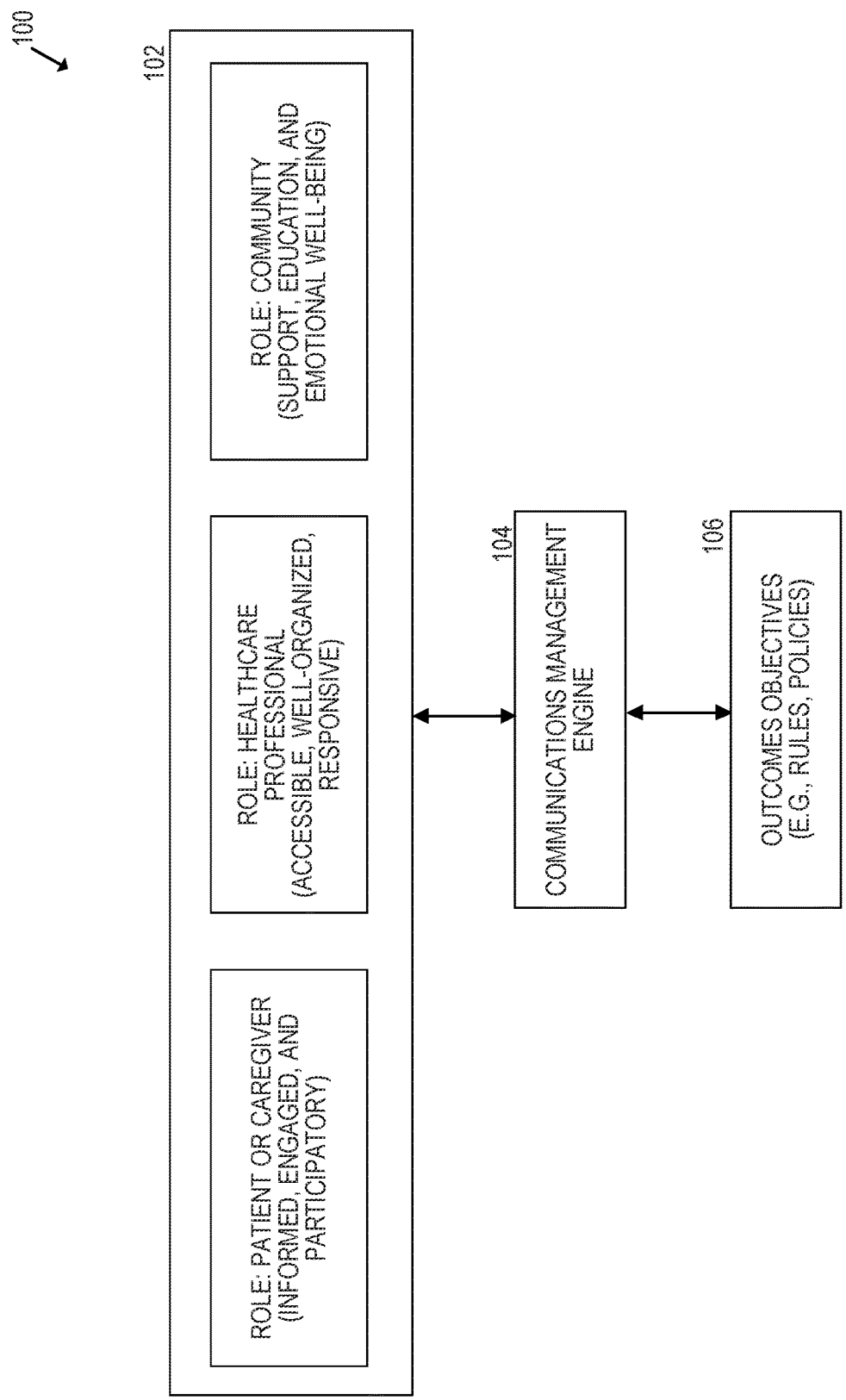
FIG. 1 is a flowchart that illustrates a process implemented by a communications centric platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

The embodiments set forth below represent necessary information to enable those skilled in the art to practice the embodiments and illustrate the best mode of practicing the embodiments. Upon reading the following description in light of the accompanying figures, those skilled in the art will understand the concepts of the disclosure and will recognize applications of concepts that are not particularly addressed herein. It should be understood that these concepts and applications fall within the scope of the disclosure and the accompanying claims.

Embodiments may be described with reference to particular computer programs, system configurations, networks, etc. However, those skilled in the art will recognize that these features are equally applicable to other computer program types, system configurations, network types, etc. For example, although the term "Wi-Fi network" may be used to describe a network, the relevant embodiment could be deployed in another type of network.

Moreover, the disclosed technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device (e.g., mobile phone, a network-connected computer server) to exchange communications, classify data items to determine an appropriate action, and perform the appropriate action.

Terminology

The purpose of terminology used herein is only for describing embodiments and is not intended to limit the scope of the disclosure. Where context permits, words using the singular or plural form may also include the plural or singular form, respectively.

As used herein, unless specifically stated otherwise, terms such as "processing," "computing," "calculating," "determining," "displaying," "generating," or the like, refer to actions and processes of a computer or similar electronic computing device that manipulates and transforms data represented as physical (electronic) quantities within the computer's memory or registers into other data similarly represented as physical quantities within the computer's memory, registers, or other such storage medium, transmission, or display devices.

As used herein, terms such as "connected," "coupled," or the like, may refer to any connection or coupling, either direct or indirect, between two or more elements. The coupling or connection between the elements can be physical, logical, or a combination thereof.

References to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to").

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing multiple tasks.

The term "managed communications" broadly refers to a form of structuring communications among members of a group to, for example, aid in achieving a desired outcome. In one example, a communications centric platform provides pipelines for structuring communications between a patient and a caregiver. For example, the pipelines can bifurcate secure and unsecure information such that information is securely shared between a patient and a caregiver in a seemly open environment. As such, the patient and caregiver engage in structured communications that seem natural.

When used in reference to a list of multiple items, the word "or" is intended to cover all of the following interpretations: any of the items in the list, all of the items in the list, and any combination of items in the list.

The sequences of steps performed in any of the processes described herein are exemplary. However, unless contrary to physical possibility, the steps may be performed in various sequences and combinations. For example, steps could be added to, or removed from, the processes described herein. Similarly, steps could be replaced or reordered. Thus, descriptions of any processes are intended to be open-ended.

The disclosed embodiments include a communications centric platform ("platform") that manages communications in a structured manner to advance members of a group towards a common objective. Examples of the communications include electronic text, images, or the like. In one example, the platform initiates and manages an instant message dialogue between computing devices of a patient, caregiver, or other members of a group. The communications conform with a schedule of structured events to achieve an improved health outcome for the patient.

The platform can identify a suitable disease management journey for a particular patient, where the journey includes a schedule of key events typically experienced by similarly situated patients. For example, a machine learning model can process user-generated data to identify a likely journey for a patient from among multiple journeys. The journey has a particular structure of key events to stage timely content that may be personalized for a patient's recovery. The platform also allows users to create closed communities (e.g., including loved ones, peers, mentors) that foster hope, engagement, and emotional well-being at points in time of key events to help advance the common objective of improving the health outcome of the patient.

That is, the platform connects members of the closed group with other members to form larger support networks that aid in advancing multiple objectives. For example, the platform can help connect caregivers of different closed groups to create practical and emotional support networks that address caregiver health and well-being concerns. The platform can further serve to reassure and build confidence in caregivers that feel alone, overwhelmed, and responsible for making difficult decisions.

The platform can also help educate members of groups. In particular, the platform can help patients regain a sense of control over their care by educating on next steps that can reduce unnecessary visits and readmissions. The platform also engages and activates members of a group. For example, the platform improves engagement by helping patients and caregivers to create meaningful relationships with managed communications. As a result, the platform improves patient experience by integrating with systems and resources to create a connected, seamless treatment that drives user stickiness and loyalty while managing communications to achieve a collective objective.

FIG. 1 is a flowchart that illustrates a process implemented by a communications centric platform. As shown, the platform separates users into roles 102, where each role has one or more data access rights and provides certain communications. A patient role or caregiver role can have a first set of data access rights that include access private healthcare data and private personal data. The patient can have control over who gets granted access to the private data. The patient can grant a caregiver with access to certain private data. The communications from users in this role are managed to keep other users informed, engaged and participating in the patient's disease management.

A healthcare professional role (e.g., doctor) can have a second set of data access rights that are different from the first set of data access rights. For example, the healthcare professional can have access to private medical data while being denied access to personal communications of the patient that are part of the recovery process. The communications of users in this role are managed to keep data accessible, well-organized, and responsive.

A community role can have a third set of data access rights that are different from the first and second sets of data access rights. For example, the community role may not have any automatic data access right. Instead, a user with a community role can only see data that is directly shared by the patient or caregiver. In other words, the community role does not have any independent visibility into communications. The communications of users in this role are managed to provide support, education, and emotional well-being of other users.

The communications from users of different roles 102 are processed through a communications management engine 104 ("engine 104"). The engine 104 functions to harmonize the communications (e.g., messages, data) to conform with the structure of the journey of a patient's recovery. For example, users in the community role may communicate freely with both patients and caregivers to provide support and education. In contrast, users that are healthcare professionals may only communicate with the patient and authorized caregivers to maintain the patient's privacy. The engine 104 is operated in accordance with outcomes objectives, which can include rules, policies, conditions, etc. Thus, the outcomes objectives drive the communications management engine 104 to manage the communications of users that have different roles 102. The management of communications is based on the structure illustrated in FIG. 1 and prioritizes those building blocks in a manner that improves communications for care teams of patients and caregivers.

Figure 2:
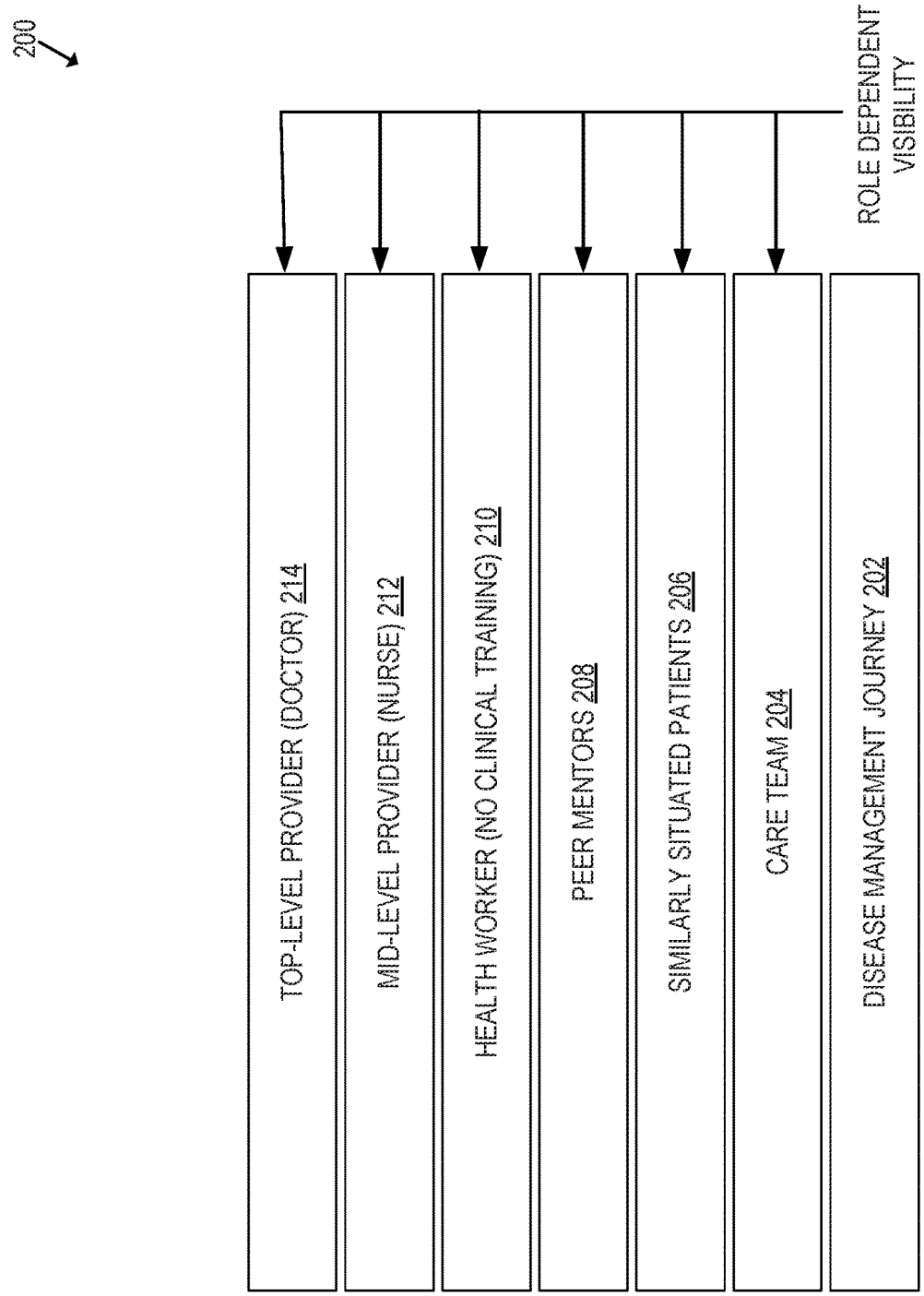
FIG. 2 is a block diagram that illustrates an layered architecture of the platform.

FIG. 2 is a block diagram that illustrates a layered structure of the platform 200. As shown, a foundational layer for managed communications is the journey 202, which is based on a disease management plan. The communications of the care team 204 (e.g., patient, caregiver) are managed in accordance with the journey 202. A similar patients 206 layer is above the care team 204, and a peer mentors 208 layer is above the similar patients 206. The similar patients 206 layer includes users of the platform that are simultaneously having a similar experience as the patient, and the peer mentors 208 layer includes users that have already had a similar experience as the patient. The layering can define the level of access rights to data or degrees of visibility into data. For example, peer mentors 208 can have less visibility to private data compared to the care team 204. The layers above the peer mentors 208 include a health worker 210, mid-level provider 212, and top-level provider 214.

The engine can bridge communications between the home-side interconnections and service-side interconnections. In some embodiments, the health worker population or any of the healthcare providers can be virtual providers. In one embodiment, the platform can manage communications with role dependent visibility. That is, user interfaces of the platform can vary for each role such that a doctor has a view of an interface that presents information that identifies the patient whereas the view of the interface for a health worker may only provide access to non-identifying information.

Figure 3:
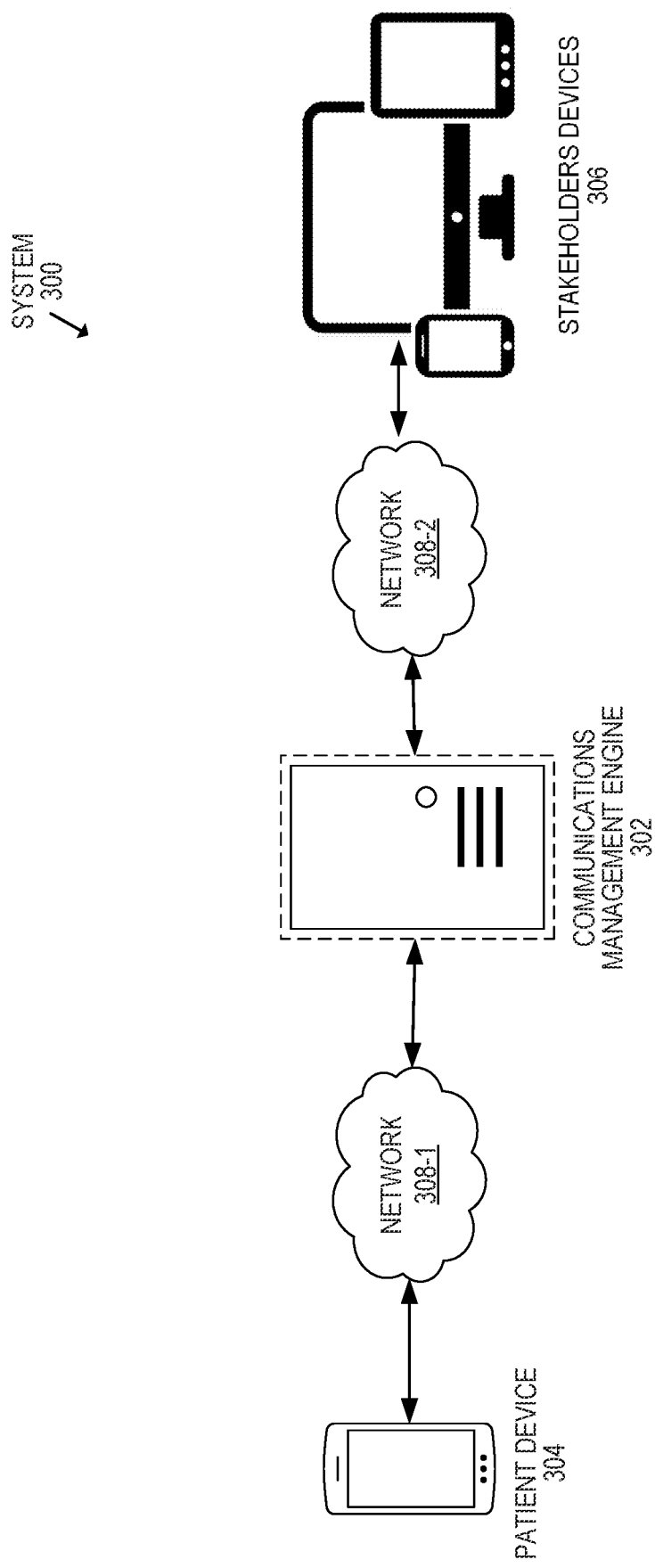
FIG. 3 is a block diagram that illustrates a system that implements the platform.

FIG. 3 is a block diagram that illustrates a system 300 that implements the platform. The system 300 manages communications that are shared on devices operated by the patient and other stakeholders of a disease management journey. As shown, the communications management engine 302 ("engine 302") can manage communications that are shared among a patient device 304 and other stakeholder devices 306 over networks 308. The engine 302 may administer a mechanism that improves the engagement by the patient of the patient device 304 to complete a communication flow between a patient and caregiver. In some embodiments, the mechanism could be part of a portal that allows users to exchange information related to a patient's medical condition. Examples of the portal include a website, mobile app, or any communications mechanism.

The engine 302 can implement a disease management journey that is customized for a patient by applying information about the patient to algorithm(s). For example, the patient's background information and contextual information can cause the communications management engine to control information that is available to stakeholder devices 306. In some embodiments, contextual information could be derived from user inputs and applied to algorithm(s) to improve the communications management. Further still, information obtained from sources other than patient device 304 can be used to engage the patient to provide additional useful information for algorithm(s) that implement the journey.

Each component of the system 300 may include combinations of hardware and/or software to process data or information, perform functions, communicate over the networks 308, etc. For example, any component of the system 300 may include a processor, memory or storage, a network transceiver, a display, OS and application software (e.g., for providing a user interface), and the like. Other components, hardware, and/or software included in the system 300 that would be well known to persons skilled in the art are not shown or discussed herein for the sake of brevity. The networks 308 can include any combination of private, public, wired, or wireless portions. The data or information communicated over the networks 308 may be encrypted or unencrypted at various locations or along different portions of the networks 308.

The patient device 304 and stakeholder devices 306 (collectively referred to as "user devices") can exchange communications over the system 300 through the communications management engine 302. Examples of patient devices 304 and stakeholder devices 306 include smartphones (e.g., GOOGLE PIXEL, APPLE IPHONE, SAMSUNG GALAXY), tablet computers (e.g., APPLE IPAD, MICROSOFT SURFACE), computers (e.g., GOOGLE CHROMEBOOK, APPLE MACBOOK, LENOVO THINKPAD), and any other device that is capable of exchanging data with the over the networks 308. For example, a mobile device operated by a patient can communicate with a caregiver via a disease management app running on the patient device 304.

The user devices can include a global positioning system (GPS) receiver that receives positioning signals used to determine the geographic location of the user device. The determined geographic location can be submitted to the engine 302 to influence selection of a recommended screen view for a patient or stakeholder based on the location of the user device. For example, an automatic communication could be invoked on the patient device 304 when the location of the patient device 304 is a hospital.

The engine 302 may execute on any number of server computers that operate to perform processes such as determining a journey based on inputs and contextual information related to a patient's health condition. The engine 302 operates to engage users of the user devices in accordance with a communication mode. The collected data and/or information is managed to further the patient and stakeholders towards an outcome. The engine 302 can execute algorithms for managing communication flows among patients and other stakeholders. For example, a communication algorithm may include a combination of rules for selecting types and forms of communications for the patient at a particular point in time of a patient's journey.

A set of rules of a communication management algorithm can customized for the patient's disease management journey as prescribed by a healthcare professional. A communication management algorithm may include a combination of rules for selecting a suitable communication flow. In some embodiments, any of the disclosed algorithms may include policies having rules, criteria, conditions, and/or thresholds that are set in accordance with a disease management protocol to apply the policies in a manner that is personalized for a patient. For example, a communication algorithm may include a rule set based on a first patient's gender, age, and a diagnosed condition. Another communication algorithm for a second patient may include a different set of rules based on that patient's demographics.

The data input by a user of a user device engaged in a communication-centered care may be communicated automatically to the patient's healthcare provider upon establishing a direct connection so that the healthcare provider can seamlessly aid the user. Accordingly, data from healthcare providers, other devices, or services can be provided by the stakeholder devices 306 over the networks 308 through the engine 302.

The stakeholder devices 306 may include any number of servers or other computing resources that can collect, store, and/or provide data or information to the engine 303 over the networks 308 for use in the care of a patient. The stakeholder devices 306 may include any source of health-related information. For example, the stakeholder devices 306 may include any devices operated by providers such as medical facilities, private offices, or devices administered by healthcare professionals. In some embodiments, the data or information may include at least portions of medical records utilized in medical algorithms. The stakeholder devices 306 may include contextual information related to or affecting the diabetic condition of a patient obtained from a variety of devices.

Figure 4:
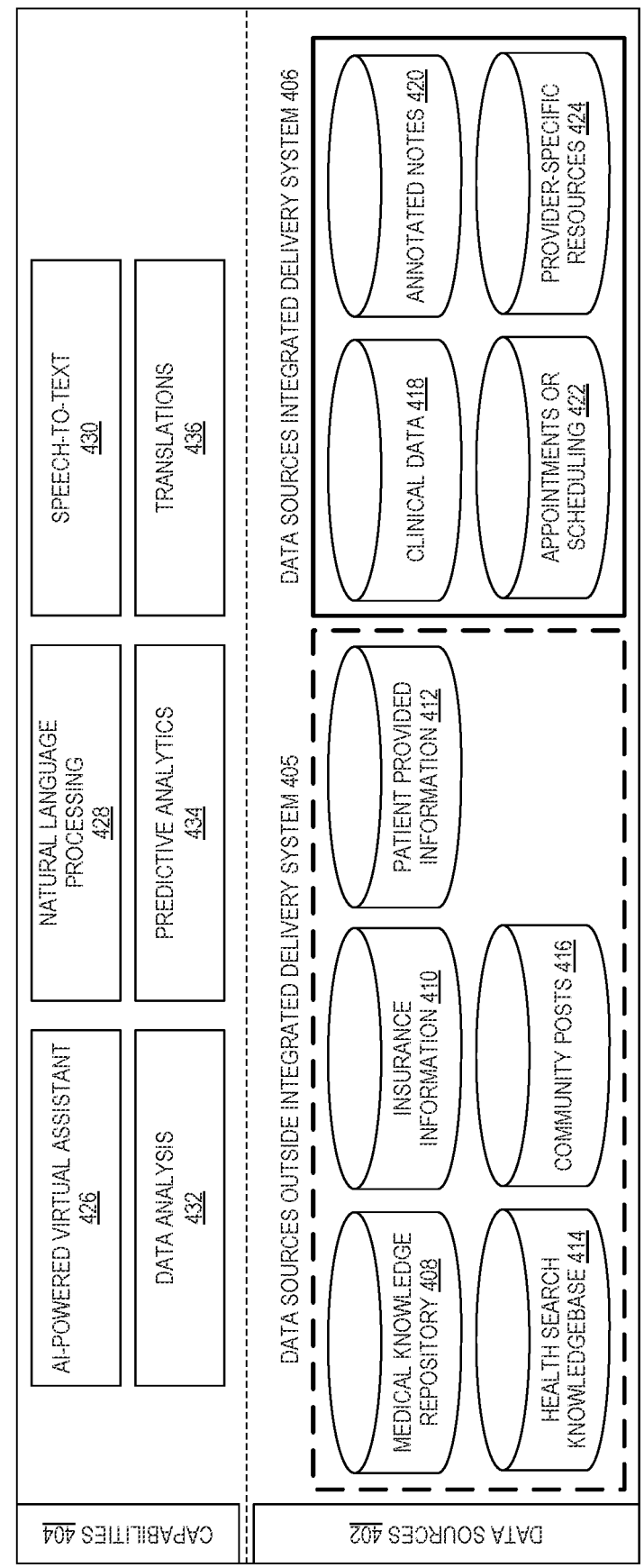
FIG. 4 is a block diagram that illustrates an architecture of a communications management engine.

FIG. 4 is a block diagram that illustrates an architecture 400 of a communications management engine. The platform can leverage capabilities of other features or products to improve usability. This includes integration of machine learning capabilities to obtain medical data and identify potential issues, integration with search engines to search for relevant health related data, a natural language processing interface for search and data structure for content, the ability to pull data from third party devices such as fitness devices, instant messenger capabilities including chat-based conversation tools, communication user interfaces (e.g., both visual and interactive), and experience in a combination of both chatbot and a human-chat interface.

The architecture 400 includes data sources 402 that are accessible for capabilities 404. The data sources 402 include a data sources outside the integrated delivery system 405 ("outside data sources 405") and data sources of the integrated delivery system 406. The outside data sources 405 include a medical knowledge repository 408, insurance information 410, patient provided information 412, health search knowledgebase 414 and community posts 416. The data sources of the integrated delivery system 406 include clinical data 418, annotated notes 420, appointments or scheduling 422, and provider specific resources 424.

The capabilities 404 include an AI-powered virtual assistant 426, natural language processor 428, speech-to-text 430, data analysis 432, predictive analytics 434, and translations 436. As such, the platform can integrate home based features and service providers. For example, on the home-side, the platform can display journey-specific content based on a user role, help coordinate activities amongst caregivers, connect to home devices and generate alerts, control home devices, and display device captured data in a profile. On the provider-side, the platform can link with electronic medical record data sources to obtain labs and imaging data, suggest and store questions for a care team, capture and track care data, and create provider facing profiles including symptoms.

The platform manages the communications of a patient and the patient's caregiver to engage in a manner that conforms to key events of the patient's disease management journey. The communications are managed to foster strong, meaningful relationships to keep users coming back to continue conversations. The disclosed embodiments enable discovery of journeys for users to experience effective treatment through managed communications among a care team. This is accomplished in part by creating a detailed and robust catalogue of disease-specific journeys. The platform can accurately place patients and caregivers on effective journeys and offer personalized guidance along those journeys based on where the patients are in their disease management.

For example, consider a case where a patient is diagnosed with a disease such as prostate cancer. When undergoing routine screening, a patient may have had a prostate-specific antigen (PSA) screening, as well as a digital rectal exam (DRE). An abnormal PSA screening could lead the doctor to recommend further testing and send the patient to a specialist such as a urologist. The patient's pathology report may then show a Gleason score of 7 (3+4), and 2 of 12 cores are positive.

This type of diagnosis could leave a patient feeling overwhelmed and scared. A caregiver, such as the patient's spouse, may start to worry about how he or she can help the patient while the doctor is discussing the diagnosis and treatment. The caregiver knows nothing about this diagnosis-only that it will test his or her ability to learn, give care, and be supportive. In these circumstances, effective communications between the patient and caregiver can make a substantial difference in the patient's treatment.

Figure 5:
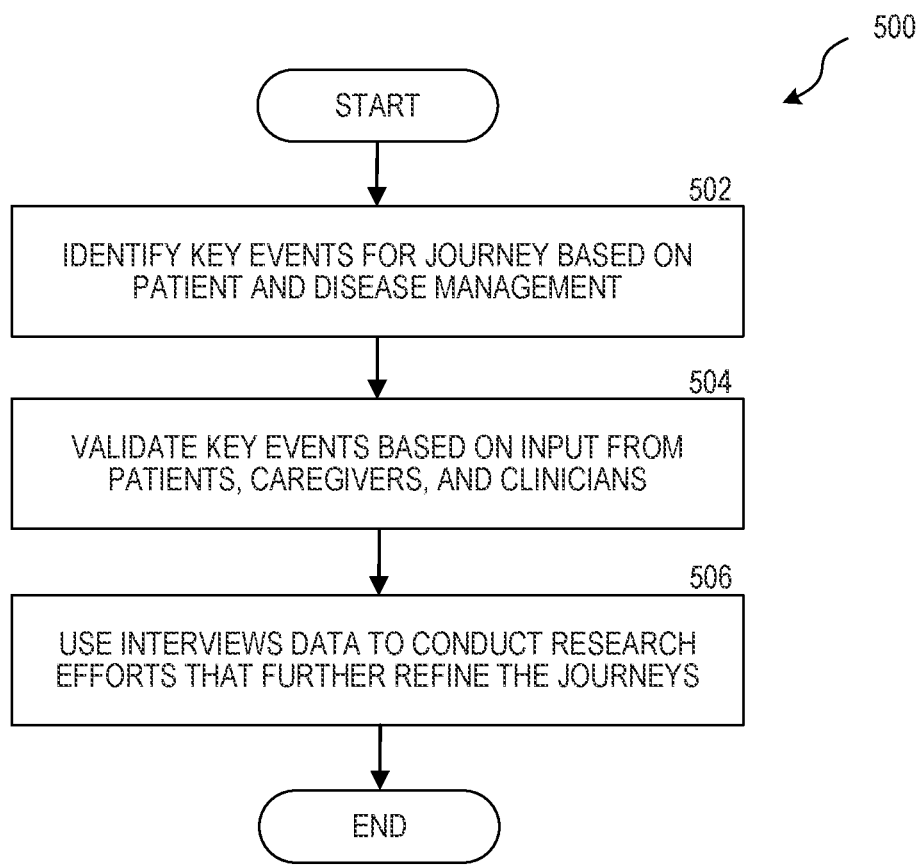
FIG. 5 is a flowchart that illustrates a process for building journeys for different diseases.
Figure 6A:
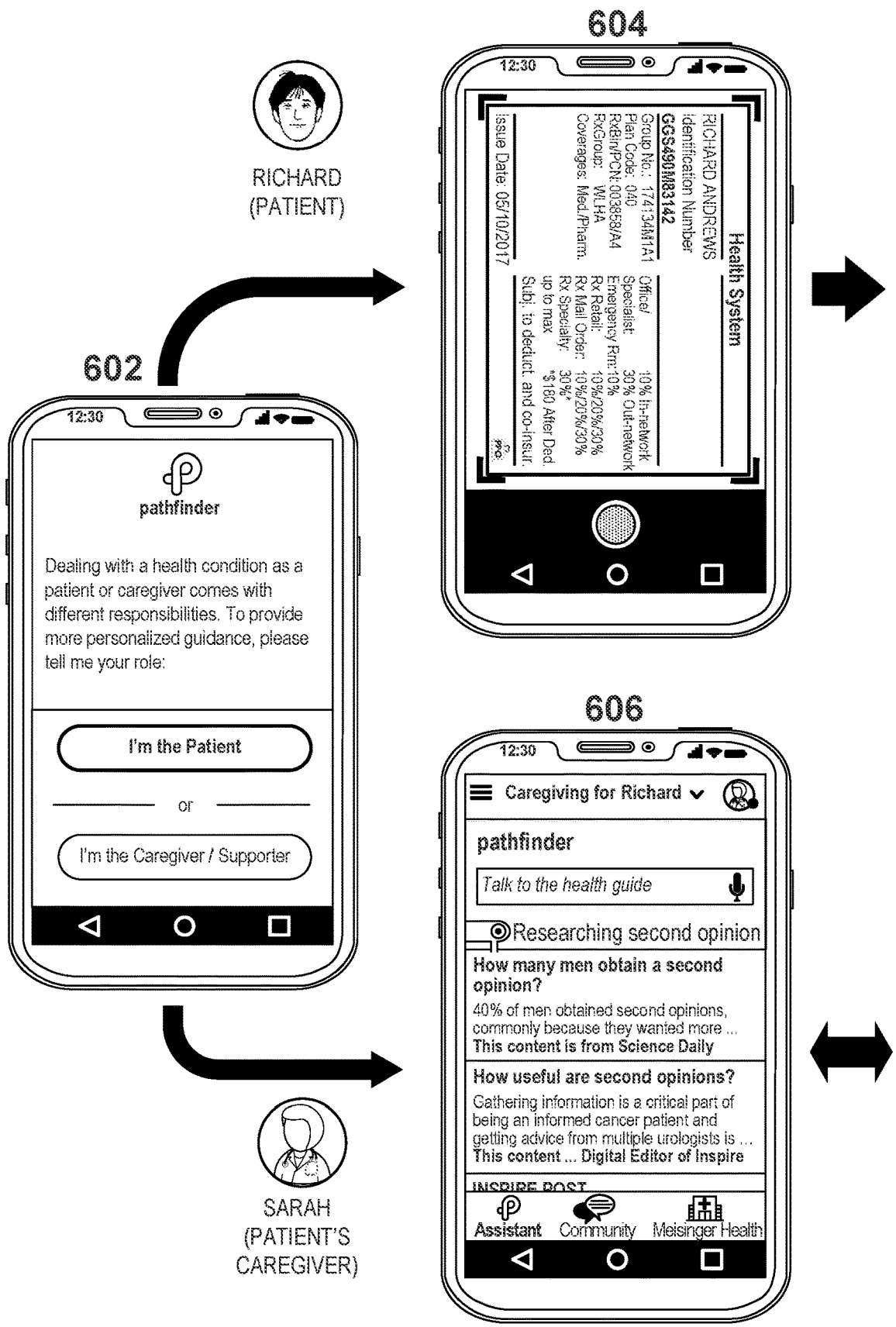
FIGS. 6A through 6D show side-by-side screen views of managed communications that are bifurcated for a patient and a caregiver.
Figure 6B:
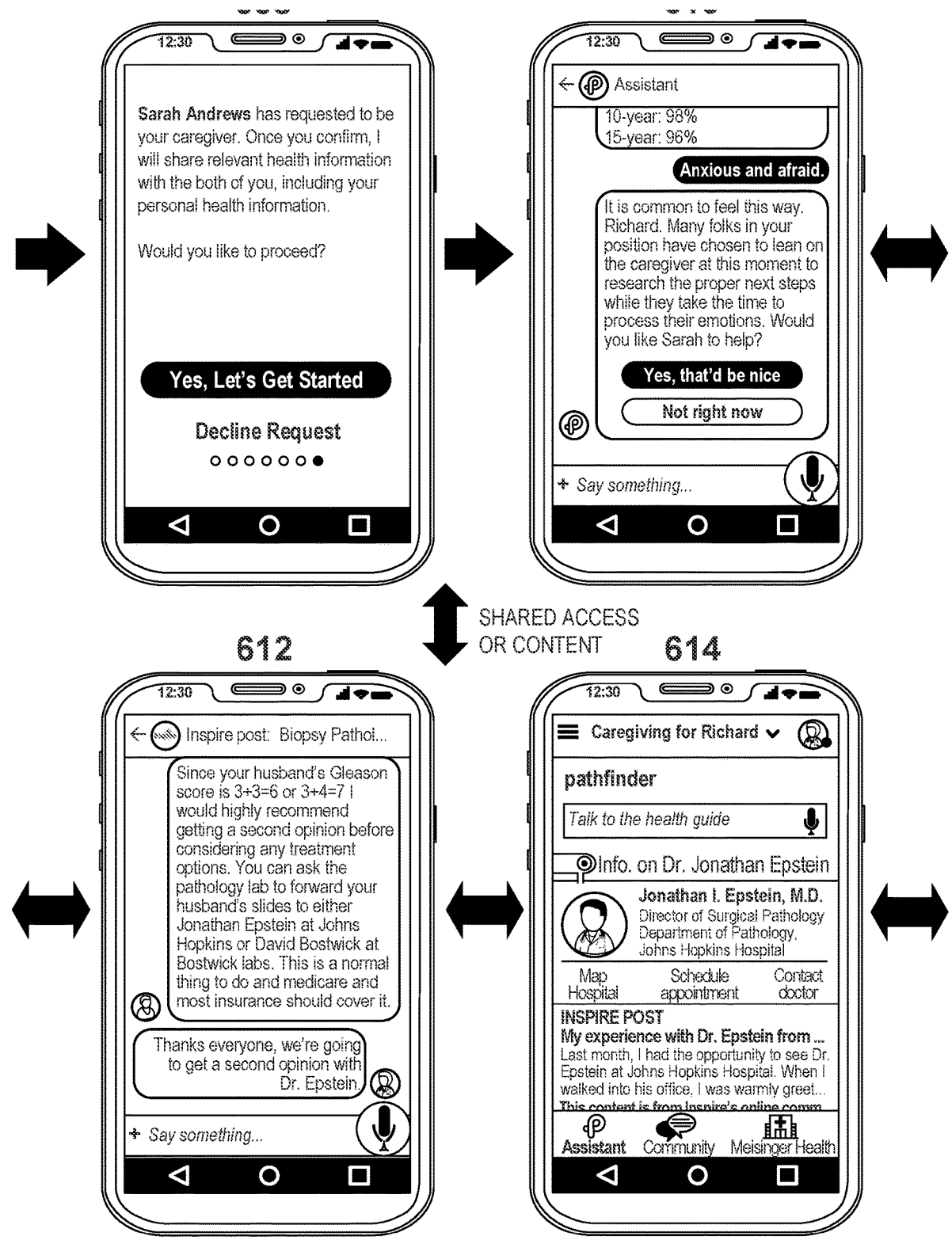
Figure 6C:
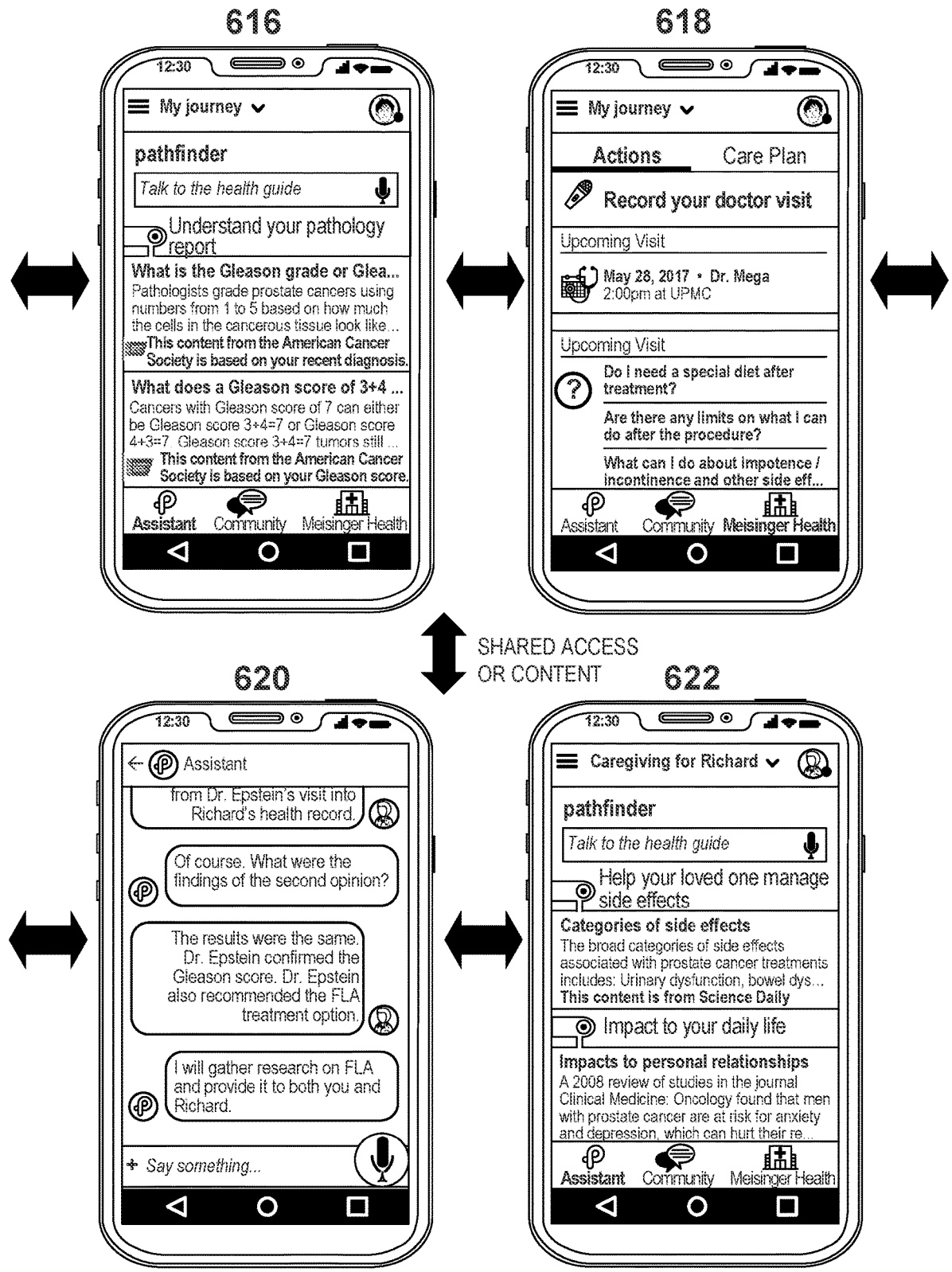
Figure 6D:
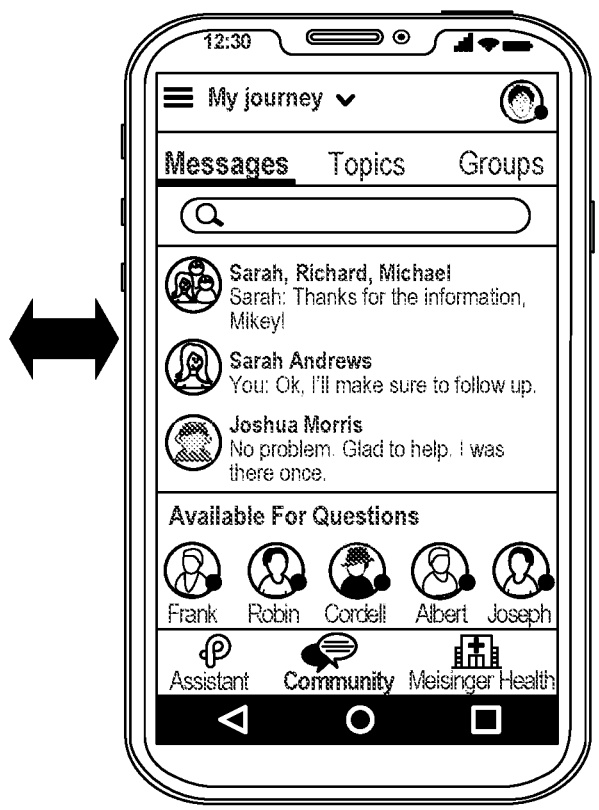

FIG. 5 is a flowchart that illustrates a process for building journeys for different diseases. The journeys represent particular implementations of disease management processes. Examples of illnesses that disease management would concern itself with would include coronary heart disease, chronic obstructive pulmonary disease (COPD), kidney failure, hypertension, heart failure, obesity, diabetes mellitus, asthma, cancer, arthritis, clinical depression, sleep apnea, osteoporosis, and other common ailments. A journey is personalized for a patient and the patient's specific disease. The journeys for particular diseases are further customized for particular patients.

In 502, the platform identifies key events of diseases. The events can be curated manually based on research as a set of key events for one or more diseases. Examples of key events include a schedule of treatments, medical appointments, tests, diagnostics, and any other event that normally occurs as part of disease management. The key events can be identified by utilizing machine learning based on historical interactions of other patients with similar diseases.

In 504, the platform validates the key events with patients, caregivers, and clinicians. For example, the platform allows patients, caregivers, and clinicians to share information of hand-curated journeys that can be used to validate the key events. The patients, caregivers, and clinicians can also provide feedback to created journeys to validate the key events.

In 506, the platform can use survey or interview data to conduct further research. The interviews can be with patients and caregivers. The interview data can be extracted from posts and analyzed by using natural language processing to extract meaningful information. In some embodiments, the interview information could be with providers or based on electronic medical record (EMR) data (e.g., clinical notes and claims data). As such, the journeys can be built and refined to improve communications management by the platform.

The platform stages communications and content. In one embodiment, the platform is embodied as a system that provided a patient centric interface for a patient and a counterpart caregiver centric interface for the patient's caregiver. The patient and the patient's caregiver experience different interactive interfaces to help navigate both individuals along a journey of recovery in a manner that is applicable to their specific roles relative to the patient's treatment. For example, the platform provides different communication tools at different points in the journey for the patient and caregiver while guiding them as a care team that is collectively on the same path towards the patient's recovery.

The platform includes a means to facilitate exchanging communications between a patient and caregiver. For example, the patient and caregiver can install mobile apps on their handheld devices (e.g., smartphones) that present interfaces that are customized for respective roles while keeping the care team on a common journey towards the patient's recovery.

FIGS. 6A through 6D show side-by-side screen views of managed communications that are bifurcated for a patient and the patient's caregiver. In the illustrated embodiment, an app administered or controlled by the platform is running on mobile phones of the patient and the caregiver. The platform controls the communications over the mobile devices via the apps to stage the way that the patient and caregiver engage as they advance through a journey.

Each screen view is part of an interface that includes various features for setup and onboarding of users and categories of features under different tabs that are accessible by the care team. For example, the tabs can include an "Assistant Tab," a "Support Tab," and an "Integrated Delivery System Tab." The integrated delivery system integrates with medical care systems to provide care delivery and health insurance information for a population of patients in a defined geographic region. Each category of features includes different items to facilitate communications centric care. The communications are controlled to induce shared decision making where patients and family members are involved in decisions early. The decisions can relate to end of life care and can help a care team make appropriate treatment decisions.

Screen view 602 is an initial screen view to onboard Richard as a patient and Sarah as Richard's caregiver. This initial screen view can include a log-in screen that ask the patient and caregiver which role they have as part of a care team. The patient selects the "I'm the patient" role, while the caregiver selects the "I'm the caregiver/supporter" role. Once selected, the platform establishes communications pathways for managing communications for the different members of the care team. The platform processes input by the patient and caregiver in accordance with their roles at each key point along the journey. The communications management engine can personalize communications for each member of the care team in accordance with their roles.

By managing the communications in a controlled manner, the platform can ensure that the patient and caregiver communicate effectively in their respective roles at key events along the journey. As such, the members of the care team can collaboratively improve the health outcome of the patient. Despite having different roles, the platform can aid each member to communicate effectively as a team by ensuring that communications occur at a timely manner with respect to key events of a journey.

The platform can also leverage experiences of other patients or caregivers so that members of multiple care teams can learn from others. For example, community screen views for members of the care team can aid an individual member to identify similarly situated individuals in a group which the care member could benefit from by joining. The platform may identify a patient group (or form a group) with other patients that face the same condition and decisions at the stage of recovery. Likewise, the platform may identify a caregiver group (or form a group) with other similarly situated caregivers that face similar challenges.

The platform makes it easy for the patient to connect to his medical records. For example, the patient can connect the platform to his medical records by taking a photograph of his healthcare insurance card. Screen view 604 illustrates using a smartphone's camera, on which the care app is running, to capture an image of a healthcare insurance card. After capturing the photograph, the platform can process the image to identify the user's EMR and access the medical records to, for example, track the user's doctor visits.

A screen view can ask the patient if he seeks assistance with a recent medical event and include a selectable control for a diagnosis. As such, the platform utilized the patient's medical records to provide more timely feedback rather than needing the patient to input basic information about his health status. The patient can confirm that he would like assistance from the platform for his recently diagnosed disease rather than some other medical event identified in his medical records.

Screen view 608 shows an authorization screen for the patient to authorize the caregiver. As such, a caregiver role is granted by the patient before the caregiver can interact with the patient over the platform in that capacity. After these initial onboarding screen views, the platform can also provide a general or role-specific tutorial to teach a care team member how to effectively utilize the platform to improve communications as one team. The tutorial can guide the patient through how to use the platform. For example, the tutorial can guide the patient to learn about tabs including an "Assistant" tab, a "Community" tab, etc.

In some embodiments, the screen views can welcome the patient with useful information presented in a conversational format. That is, the patient is brought into a conversation with his new health assistant. The platform starts with some information that is both reassuring and human. A research-based screen view of information can be provided to the patient as well. The information could be general information or disease-specific and/or role-specific. As such, for example, the patient can process the information that the platform provides. When the patient sees data attributed, for example, to the American Cancer Society, the patient starts to feel that the platform can offer credible information to him.

The platform can also proactively ask the patient how the patient is feeling. The patient appreciates that the platform is anticipating some of the questions that the patient has. The patient can evaluate a list of options and choose a selection. In one example, the patient selects the "Anxious and afraid" option. The patient's feedback aids the platform to engage the patient in a conversational way that is empathetic to the patient's emotional and mental state.

Screen view 610 includes suggested useful next steps that leverage the caregiver. That is, the platform is actively inducing the patient to engage the caregiver in accordance with a key point of the patient's journey. The engagement by the platform mimics a human's supportive conversations.

Normally, a patient would not proactively ask the caregiver for help. As such, the platform serves as a bridge between the patient and the caregiver, which encourages effective communications at particular key events in time. Notably, the interactions between the patient and the platform appears on the screen view as a chat conversation that combines factual information, survey information, feedback, etc. that results in an overall conversational flow format.

The platform can identify a group of similarly-situated individuals that have recently dealt with the same condition and are in the patient's geographic area. A screen view may include a clickable link or another mechanism to prompt the patient to communicate with the group. The patient may appreciate that the group has been identified but nevertheless decide to not yet communicate with similarly-situated patients. Instead, the patient may want to read more about his disease on his own. In that case, the patient may click on a back arrow in an upper left-hand corner of a screen view to view a resource of information.

Screen view 616 includes content cards that are curated for the patient based on where the patient is on his path to recovery. Because the patient recently received his pathology report, which is a key event, the platform has identified specific cards to help the patient understand his pathology report. Hence, the selection and/or combination of content cards can be personalized for the patient and his Gleason score.

For a caregiver, the platform provides a series of role-specific screen views to facilitate effective communications with the patient. Screen view 606 provides information that is specific for the caregiver and includes relevant content from different resources. For example, the caregiver can be alerted by the platform later that day to help the patient to research second options. The platform can deliver a set of useful content cards that helps lead the caregiver to a post as a resource for a second opinion. That post is relevant to the care provided by the caregiver to the patient.

The series of screen views allow the caregiver to quickly connect with individuals that can offer advice based on personal experience. For example, the caregiver can ask questions of people linked to a posted resource. Screen view 612 shows responses from other individuals in the group. This allows the caregiver to get advice based on personal experience, to provide care to the patient. The caregiver receives responses from a community of similarly-situated caregivers and the name Dr. Jonathan Epstein is identified. The caregiver can receive a recommendation from individuals in her geographic area to see Dr. Epstein. The caregiver can seek to find out more information about Dr. Epstein and ask the platform for help to obtain that information.

Screen view 614 shows information about Dr. Epstein. This screen view allows the caregiver to schedule an appointment with Dr. Epstein. The platform then updates the content cards on her home screen with Dr. Epstein's information. A screen view can present the caregiver sharing the latest clinical results with the platform a week later, after the visit with Dr. Epstein.

Screen view 620 shows treatment options for the caregiver. That is, the platform can predict treatment options at stages of the patient's path to recovery and, as such, can preemptively pull together new content on the topic for the caregiver and the patient. When the caregiver confirms the diagnosis and is ready to move on to considering treatment options, the platform can respond accordingly.

A series of screen views for the patient can identify treatment options. For example, the patient may want to learn more about FLA and robotic surgery from individuals that have undergone similar treatment. The platform can find suitable individuals for the patient to connect with for assistance. After researching his treatment options, the patient has narrowed his options down to FLA and robotic surgery. When the patient clicks on a Community tab, the platform auto-generates a few groups for him: members who underwent both types of treatments recently as well as over a year ago. Over time, both the patient and caregiver develop new mindsets. The patient is accepting that he has cancer and the caregiver is more positive about helping the patient at a key moment in the patient's life.

The screen views can connect a patient with a group, to learn what other patients have experienced. Through the messages from the members of the community, the patient gains a beneficial perspective to face next steps in his treatment. The patient can navigate to the Topics tab and see that the platform has presented reluctant threads for the patient to engage. After chatting with online community members, the patient views the Topics tab and sees that the platform has curated a small but relevant set of posts for the patient at his specific stage in the path to recovery. After getting the information that the patient and caregiver need, they decide that FLA treatment is the best option and can begin to prepare accordingly.

Screen view 618 is a preop screen view for the patient. That is, before his operation, the patient prepares for his visit via a messenger health tab in the app.

Screen view 622 shows depicts updating content for the patient and caregiver, after treatment screen views. During the patient's treatment, the platform continues to update content for both the patient and the caregiver. For the patient, he sees content that helps him stay on top of his recovery process. For the caregiver, she sees content that will help the patient manage his side effects but also strategies to help her maintain her personal wellness. Months later, the patient has completed treatment and made a smooth recovery with the love and support of his spouse due to the effective communication that was facilitated by the platform.

Lastly, returning back to screen view of the patient, screen view 624 is for monitoring the patient's health. As the patient continues to monitor his health with more PSA tests, the patient is now a labelled survivor and can help others as well. The platform may connect him with other patients facing the same challenges and now he can be a mentor to other patients.

In some embodiments, aspects of the platform are integrated in other medical care systems to provide "personalized medicine" by enabling others to efficiently learn about the patient's disease management process, obtain current information about the patient, and provide information to the patient about similarly situated patients, to help identify a suitable journey.

In one embodiment, the platform can manage the exchanges of messages of medical care systems to control the communication of electronic messages for key events. For example, the platform can message users before scheduled visits, prompt users to review and update a profile as well as to prepare questions for healthcare professionals beforehand, provide summaries from an EMR after a patient visits a doctor, provide Google alerts for relevant content based on preferences and interest areas, and/or prompt ongoing symptom tracking and health check-ins using short questions for a patient. In some embodiments, the messages can be communicated by a home or personal virtual assistant. The platform can manage one or more diseases for a patient via a home care management platform and provide users with different interfaces that depend on their roles in care management. For example, the patient would have a user interface tailored for a patient role, and the familial supporter would have a user interface tailored for a supporter role.

Therefore, the platform can provide personalized guidance for patients and caregivers with managed communications that facilitate obtaining help for a patient by a caregiver. This includes facilitating the way in which information is shared such as research insights across family members. This can help the group, including the patient, make difficult decisions collaboratively.

Figure 7:
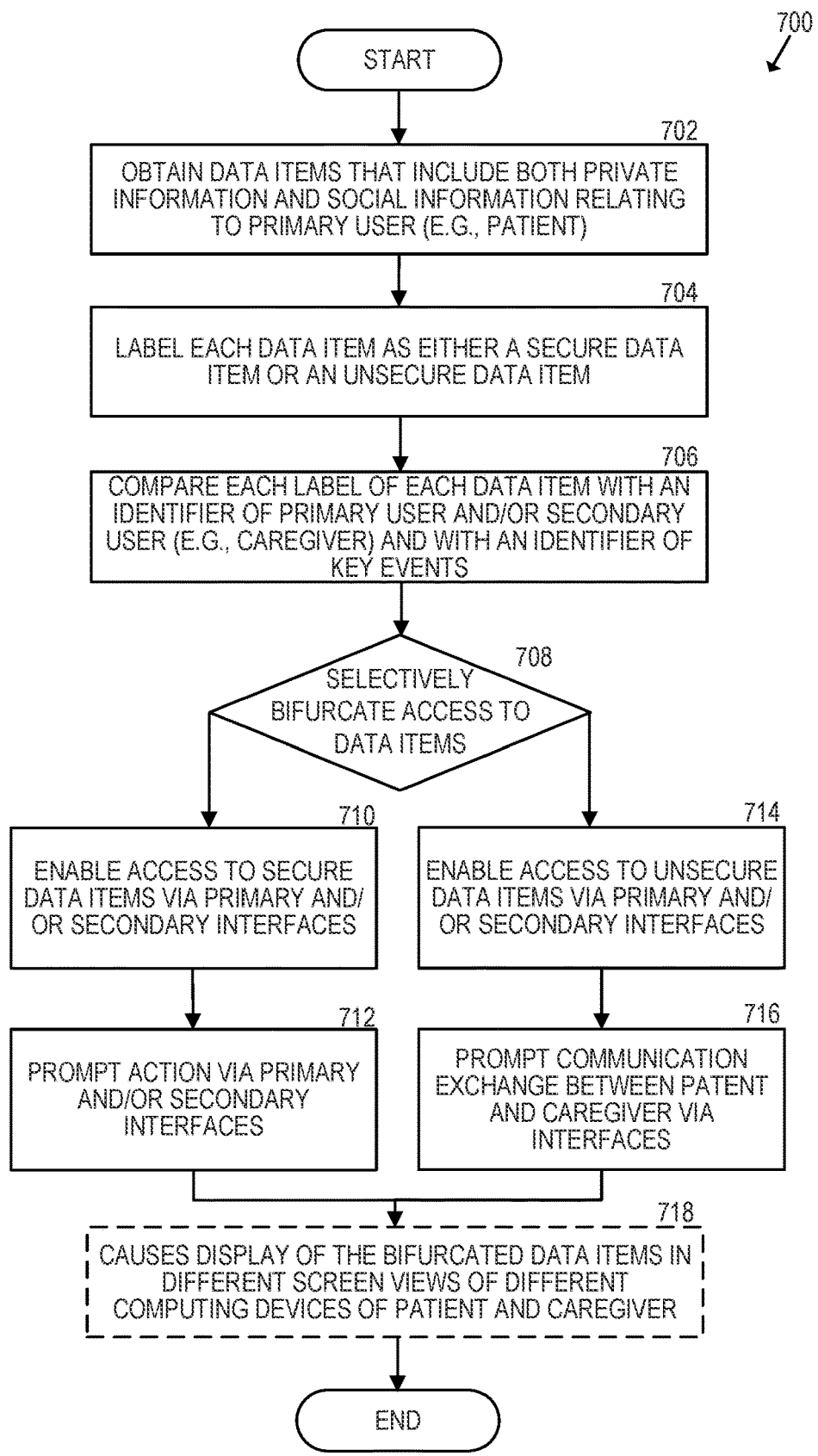
FIG. 7 is a flowchart of a process for managing communications between a patient and a caregiver.

FIG. 7 is a flowchart of a process 700 for managing communications between a patient interface on a handheld mobile device of a patient and a caregiver interface on a handheld mobile device of the caregiver. More generally, the process 700 is performed by a system that implements a platform to manage communications (e.g., in accordance with a disease management program) between a primary interface on a computing device (e.g., for a patient) and a secondary interface on a computing device (e.g., for a caregiver).

In one example, the disease management program can be selected from among a variety of disease management programs based on characteristic(s) of the patient. The system can extract the characteristic(s) from the EMR including a medical history (e.g., ongoing disease) and demographics (e.g., age, gender). The EMR can be identified based on a scanned image of a health insurance card captured by a camera of a handheld mobile device that displays the patient interface (see, e.g., screen view 604 of FIG. 6A). For example, a scanned image of the health insurance information can undergo an OCR process to extract an identifier linked to the EMR stored in a medical repository.

In 702, the system obtains data items (e.g., content items) that can include both private information and social information relating to the primary user. In an example, the private information is obtained from a private source or from the primary user as input that designates a data item as private information. In another example, the private information is obtained as input from the primary user that designates the data item as private. Other examples of private information include medical information from the EMR or personally identifiable information such as a social security number. Examples of social information include information that users typically post on social media networks to describe themselves to others.

The caregiver interface serves the patient interface in accordance with key events of the disease management program. The key events can be identified based on information of other patients that completed the disease management program. The key events are scheduled for different points in time. For example, a timeline for the key events can be determined based on the information of the other patients, where the information includes one or more key events for the disease management program. The system then schedules the key events at the different points in time in accordance with the timeline.

In 704, the system labels each content item as either a secure content item or an unsecure content item. For example, the system can label every content item of multiple content items with a respective label, label each content item multiple times, label only some of the multiple content items, etc. The secure content items include content items that can represent private information. The unsecure content items can include content items that can represent social information. The labeling can be based on a user designation. For example, a patient can designate personal information as private information that should be secured or social information that can be unsecured.

In some embodiments, the labeling is based on the source of a content item. For example, content items sourced from an EMR can be automatically designated as private information that should be secured. The source can include a general type of repository (e.g., hospital) of secure content items or a particular source associated with a policy to label content items as secure or unsecure. For example, a patient's doctor is a unique or substantially unique source (e.g., if the patient has multiple doctors) associated with an identifier. The content items submitted by the doctor are also associated with the identifier, which is used to label the content items as secure or unsecure. The identifier can include a unique character string or combination of terms (e.g. the doctor's name) that can match stored identifiers in a mapping directory that is used to label the content items.

In some embodiments, a source is based on a communication methodology used to provide content items. That is, the manner in which content items are communicated can determine a label associated with the content items. For example, content items input by a healthcare provider through a secure portal that required login credentials can be automatically labeled as secure content items. On the other hand, content items that are input through an unsecured channel where a login is not required can be automatically labeled as unsecure content items.

The social information can be obtained from a public data source. The social information can also be obtained as input from the primary user that designates the content item as social. For example, content items from the patient's social media profile can be designated as social information. Similarly, the social information can be input from the secondary user that designates the content item as social.

Labeling a content item as a secure content item can grant control of the secure data to the primary user. In contrast, labeling a content item as an unsecure content item can include automatically enabling sharing of the unsecure data with the primary user and/or the secondary user.

In 706, the system compares a label of a content item with an identifier of the primary user and/or an identifier of the secondary user and with an identifier of at least one of the key events. In one example, the system compares the label of the content item with the identifier of the secondary user only after comparing the label of the content item with the identifier of the primary user. That is, the system checks whether a content item is shareable at the key event with the primary user first before checking whether the content item is shared with the secondary user.

In 708, the system selectively bifurcates access to the content items. In one example, the system causes display of a primary screen view of a primary interface on a primary computing device of the primary user and a secondary screen view of a secondary interface on a secondary computing device of the secondary user, where the primary screen view is different than the secondary screen view. The system selectively bifurcates access to the content items for the primary interface and/or secondary interface in accordance with a combination of one or more paths. However, the paths are not limited to the combination(s) described herein. That is, the system selectively bifurcates access by (at least) one or more combinations of logical paths that are not limited to a particular combination described herein. Rather, the selective bifurcation by which content items are made accessible can be dynamic to track a particular disease management program of a patient.

In 710, the system enables access to secure content items via the primary interface (accessible by the primary user) and the secondary interface (accessible by the secondary user) in response to a label of the secure content item matching the identifier of the primary user and at a point in time in which a key event with a matching identifier occurs (e.g., only at that time).

In 712, in response to enabling access to the secure content item, the system prompts an action via the primary interface and/or the secondary interface. The "action" can include an action for a user that is separate from an interaction with the system. For example, the system can prompt the patient to modify a behavior (e.g., food consumption, exercise) or to perform another action such as scheduling an appointment with a doctor. Alternatively, the action can include a digital interaction with the system or a combination of a physical and digital action. For example, the action can include display on a patient interface of a graphical control with selectable options to schedule or reschedule a key event of the disease management program.

The system can explicitly or implicitly prompt a user to perform an action. For example, the system can prompt an action including communicating a particular selectable electronic message to a computing device of the primary user and/or the secondary user to input information related to a key event. In another example, a messaging tool is instantiated with messaging components on respective computing devices of the primary interface and the secondary interface, and a communications link is established between the computing devices. As such, the instantiation of the messaging components prompts the action of performing a digital communication exchange.

In 714, the system enables access to unsecure content items via the primary interface and the secondary interface in response to a label of the unsecure content item matching the identifier of the primary user or the identifier of the secondary user and only at a point in time in which another key event with a matching identifier occurs.

In 716, in response to enabling access to the unsecure content item, the system prompts a communication exchange via the primary interface and the secondary interface. For example, the system can cause a primary screen view to present a messaging control component on a primary computing device of the primary user and cause a secondary screen view to present a counterpart messaging control component on a secondary computing device of the secondary user. The secondary screen view can include a suggested messaging topic related to the key event of the unsecure content item. For example, the caregiver's screen view can show a suggested topic for discussing a recent doctor's visit.

In 718, the system optionally causes display of the bifurcated content items on a first screen view of a first computing device of the primary user and on a second screen view of a second computing device of the secondary user. The first screen view (e.g., patient view) is different than the second screen view (e.g., caregiver view). Thus, the patient and caregiver can have access to at least some of the same content items via their respective interfaces.

Figure 8:
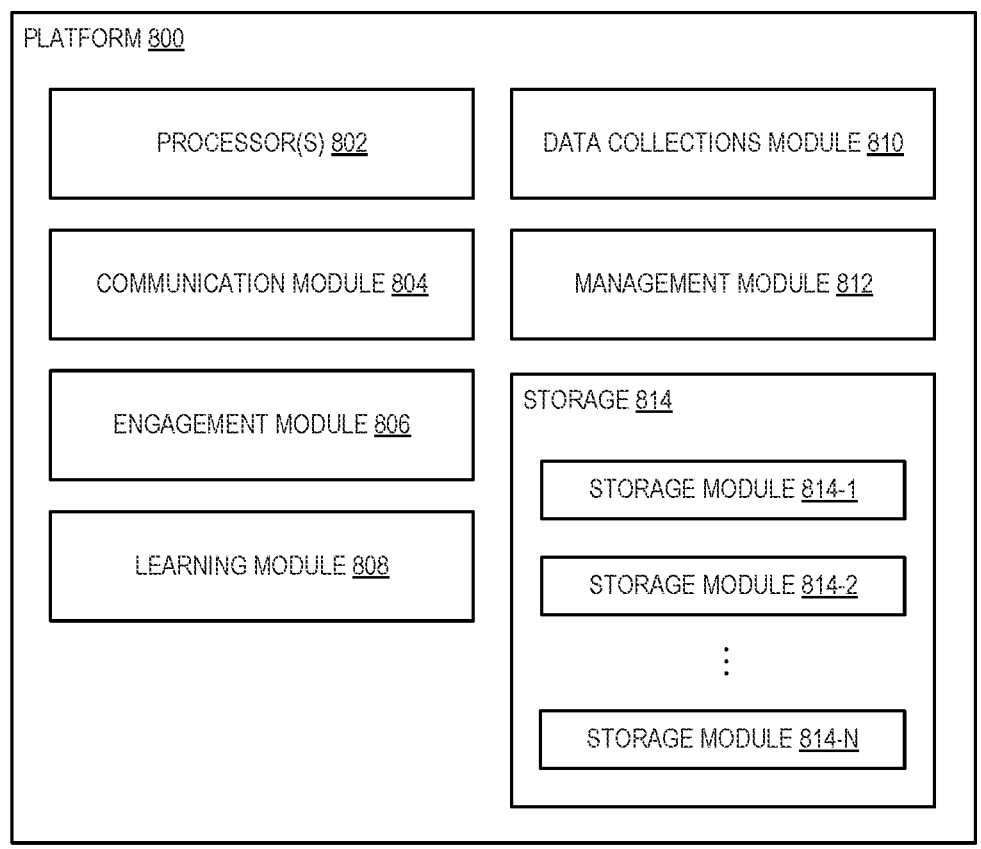
FIG. 8 is a block diagram that depicts components of the platform.

FIG. 8 is a block diagram illustrating the platform according to some embodiments of the present disclosure. The platform 800 can include components or modules that collectively operate to render screen views on communications devices for a care team as part of communications centric care. A screen view is rendered in accordance with communications centric care processes.

A communications centric care process is conducive to interactions that conform to an overarching objective to treat a patient. For example, a communication-based flow can be part of a health management process (e.g., disease management). An objective may include extracting information about a patient's symptoms and lifestyle. The screen views can be rendered on a GUI of a communication device and include a combination of graphical controls and images to maintain a user's engagement.

As used herein, a "component" or "module" may refer to a part or independent unit of hardware and/or software that performs one or more distinct functions. In some instances, a module is self-contained, separable, and/or interchangeable relative to other modules. As shown, the platform 800 includes one or more processors 802, a communication module 804, an engagement module 806, a learning module 808, a data collection module 810, a management module 812, and storage modules 814. Other embodiments of the platform 800 may include some of these modules or components and/or additional modules or components that could be derived based on this disclosure or known to persons skilled in the art but not shown herein for the sake of brevity.

The processor(s) 802 can execute modules from instructions stored in storage modules 814, which can be any device or mechanism capable of storing information. The communication module 804 may manage communication between components of the platform 800 and/or between the platform 800 and another computing device. For example, the communication module 804 facilitates communication of user inputs to a patient's health management program. The user inputs may be wirelessly uploaded by the communications device (e.g., user devices 1204) or other device (e.g., diverse sources 1206) over a network (e.g., network 1208) to a server computer.

The communication module 804 facilitates the exchange of communications between user devices and the management module 812, which controls the administration of a communication flow. The communication module 804 may transmit notifications to a user device associated with a patient or caregiver. The user input that is communicated by the communication module 804 can be stored in storage 814, one or more storage modules (e.g., storage modules 814-1 through 814-n), a remote storage accessible to the platform 800, or a combination thereof.

The engagement module 806 can generate a flow for communication-centered care. The engagement module 806 also communicates user inputs to dynamically adapt a communication flow to the user in real time or near-real time. A communication flow can be rendered on a web browser, desktop software program, mobile app, over-the-top (OTT) application, etc. Accordingly, the communication flow can be rendered on a mobile phone, tablet computer, personal computer, game console (e.g., SONY PLAYSTATION or MICROSOFT XBOX), wearable electronic device (e.g., a watch or fitness tracker), network-connected "smart" device, virtual/augmented reality system (e.g., OCULUS RIFT or MICROSOFT HOLOLENS), etc.

The data collection module 810 has access to various data sources. The sourced information is processed by the data collection module 810 in accordance with an algorithm that can be personalized for the patient based on instructions from a healthcare provider. For example, a healthcare provider can select information to deliver to a user and the order in which they should be delivered.

In some embodiments, the management module 812 can process information derived from a data source such as devices other than the patient's user device. For example, a fitness tracker worn by the patient can perform machine-to-machine communications to send the patient's fitness information to the management module 812 automatically (e.g., without user intervention).

In some embodiments, information related to communication-centered care can be stored in the storage modules 814 along with values calculated by the management module 812 based on the extracted values. In this way, the management module 812 can use the stored data to improve outputs or improve a communication flow that incorporates the obtained information or can track a user's progress or lack thereof. In some instances, the stored data could be shared with authorized users or processed with similar data or information from the other users to improve operations of the platform 800 based on the data or information of numerous users. Accordingly, the management module 812 can parse data or information and analyze extracted values of numerous users over a period of time in order to track the effectiveness of a management program, communication flow, and/or surveys.

In some embodiments, the learning module 808 can utilize user inputs and/or survey information to improve the platform 800. For example, the learning module 808 can aggregate user inputs and survey information of numerous patients and process the collected inputs or information to obtain insights about the effectiveness of certain modes of interactions, to track patients, and to adjust a communication-centered care algorithm. In some embodiments, the learning module 808 can discover new techniques for improving the effectiveness of engaging with users and improve the accuracy of existing communication flows.

For example, the learning module 808 may discover patients with certain characteristics. This learned data can be used to further personalize the way that the engagement module 806 engages users. The learning module 808 can employ various machine learning algorithms and techniques to improve the effectiveness of the engagement module 806 and/or data collection module 810. Examples of machine learning algorithms/techniques include Naïve Bayes Classifier algorithms, K Means Clustering algorithms, Support Vector Machine algorithms, linear regression, logic regression, and artificial neural networks.

In another example, communications about the patient's activities could include information used to adjust a communication-centered care process. For example, a patient's location could be determined by the GPS receiver of the patient's smartphone. The location information can be used to determine, for example, whether the patient is visiting a hospital. If so, the management module 812 can invoke a "welcome" narrative that includes a survey to collect basic health data about the user and about the reason for the visit. This collected information can be used to adjust the automated survey process.

The types of user inputs or contextual information and their sources are not limited to the examples described herein. Instead, these examples are illustrative of the diverse data types and sources that can be employed to perform an automated survey process. Unlike conventional systems that collect limited information about a patient, the disclosed technology can make use of diverse data types from diverse sources to identify how to engage a patient based on his or her particular situation or circumstances. Although not shown nor described for the sake of brevity, the platform includes modules that ensure compliance with privacy settings and data security.

Figure 9:
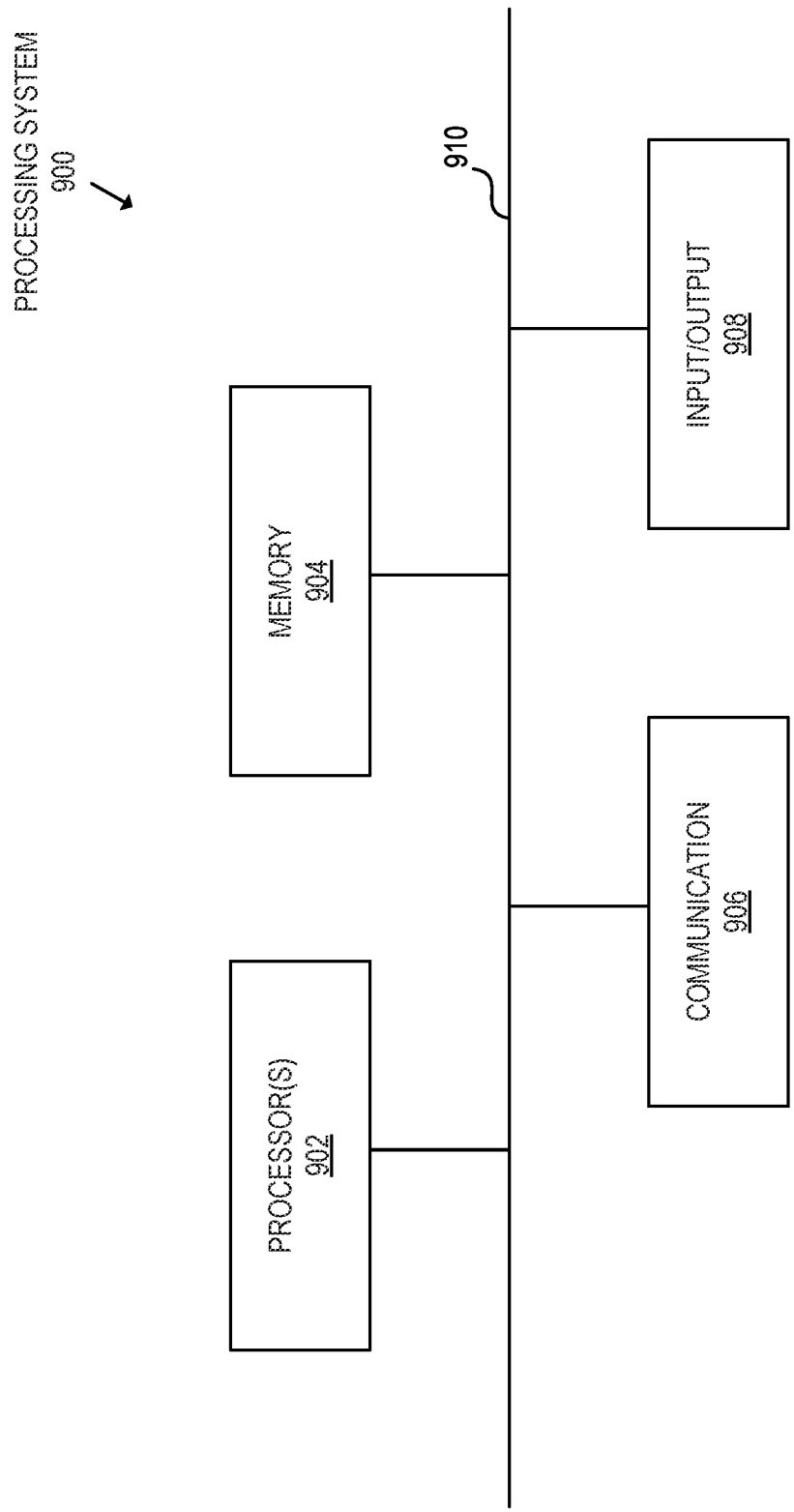
FIG. 9 is a block diagram that illustrates an example computing device in which aspects of the disclosed technology can be embodied.

FIG. 9 is a block diagram illustrating an example of a processing system in which at least some operations described herein can be implemented. The processing system 900 represents a system that can run any of the methods/algorithms described above. A system may include two or more processing devices such as represented in FIG. 9, which may be coupled to each other via a network or multiple networks. A network can be referred to as a communication network.

In the illustrated embodiment, the processing system 900 includes one or more processors 902, memory 904, a communication device 906, and one or more input/output (I/O) devices 908, all coupled to each other through an interconnect 910. The interconnect 910 may be or include one or more conductive traces, buses, point-to-point connections, controllers, adapters and/or other conventional connection devices. Each of the processors 902 may be or include, for example, one or more general-purpose programmable microprocessors or microprocessor cores, microcontrollers, application specific integrated circuits (ASICs), programmable gate arrays, or the like, or a combination of such devices.

The processor(s) 902 control the overall operation of the processing system 900. Memory 904 may be or include one or more physical storage devices, which may be in the form of random-access memory (RAM), read-only memory (ROM) (which may be erasable and programmable), flash memory, miniature hard disk drive, or other suitable type of storage device, or a combination of such devices. Memory 904 may store data and instructions that configure the processor(s) 902 to execute operations in accordance with the techniques described above. The communication device 906 may be or include, for example, an Ethernet adapter, cable modem, Wi-Fi adapter, cellular transceiver, Bluetooth transceiver, or the like, or a combination thereof. Depending on the specific nature and purpose of the processing system 900, the I/O devices 908 can include devices such as a display (which may be a touch screen display), audio speaker, keyboard, mouse or other pointing device, microphone, camera, etc.

While processes or blocks are presented in a given order, alternative embodiments may perform routines having steps, or employ systems having blocks, in a different order, and some processes or blocks may be deleted, moved, added, subdivided, combined, and/or modified to provide alternative or sub-combinations, or may be replicated (e.g., performed multiple times). Each of these processes or blocks may be implemented in a variety of different ways. In addition, while processes or blocks are at times shown as being performed in series, these processes or blocks may instead be performed in parallel or may be performed at different times. When a process or step is "based on" a value or a computation, the process or step should be interpreted as based at least on that value or that computation.

Software or firmware to implement the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM), random-access memory (RAM), magnetic disk storage media, optical storage media, flash memory devices), etc.

Note that any and all of the embodiments described above can be combined with each other, except to the extent that it may be stated otherwise above or to the extent that any such embodiments might be mutually exclusive in function and/or structure. Although the present invention has been described with reference to specific exemplary embodiments, it will be recognized that the invention is not limited to the embodiments described but can be practiced with modification and alteration within the spirit and scope of the disclosed embodiments. Accordingly, the specification and drawings are to be regarded in an illustrative sense rather than a restrictive sense.

Physical and functional components (e.g., devices, engines, modules, and data repositories) associated with processing system 900 can be implemented as circuitry, firmware, software, other executable instructions, or any combination thereof. For example, the functional components can be implemented in the form of special-purpose circuitry, in the form of one or more appropriately programmed processors, a single board chip, a field programmable gate array, a general-purpose computing device configured by executable instructions, a virtual machine configured by executable instructions, a cloud computing environment configured by executable instructions, or any combination thereof. For example, the functional components described can be implemented as instructions on a tangible storage memory capable of being executed by a processor or other integrated circuit chip. The tangible storage memory can be computer-readable data storage. The tangible storage memory may be volatile or non-volatile memory. In some embodiments, the volatile memory may be considered "non-transitory" in the sense that it is not a transitory signal. Memory space and storage described in the figures can be implemented with the tangible storage memory as well, including volatile or non-volatile memory.

Each of the functional components may operate individually and independently of other functional components. Some or all of the functional components may be executed on the same host device or on separate devices. The separate devices can be coupled through one or more communication channels (e.g., wireless or wired channel) to coordinate their operations. Some or all of the functional components may be combined as one component. A single functional component may be divided into sub-components, each sub-component performing separate method steps or a method step of the single component.

In some embodiments, at least some of the functional components share access to a memory space. For example, one functional component may access data accessed by or transformed by another functional component. The functional components may be considered "coupled" to one another if they share a physical connection or a virtual connection, directly or indirectly, allowing data accessed or modified by one functional component to be accessed in another functional component. In some embodiments, at least some of the functional components can be upgraded or modified remotely (e.g., by reconfiguring executable instructions that implement a portion of the functional components). Other arrays, systems and devices described above may include additional, fewer, or different functional components for various applications.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

While embodiments have been described in the context of fully functioning computers, those skilled in the art will appreciate that the various embodiments are capable of being distributed as a program product in a variety of forms and that the disclosure applies equally, regardless of the particular type of machine or computer-readable media used to actually effect the embodiments.

The invention claimed is:

1. A method for managing presentation of content to a first user with a disease and a second user responsible for providing care to the first user, the method comprising:
 applying, to information associated with the first user, a machine learning model that
  (i) selects a journey for the first user from among multiple journeys, each of which includes a different structure of events for staging content to facilitate managing the disease, and
  (ii) identifies an appropriate event from among a plurality of events that collectively define the journey based on a current state of managing the disease,
  wherein the machine learning model is trained based on an aggregate of data items of multiple users with the disease, and
  wherein the machine learning model is trained using a Naïve Bayes classifier algorithm, a k-means clustering algorithm, a support vector machine algorithm, or an artificial neural network;
 obtaining a plurality of data items associated with the first user;
 labeling each data item of the plurality of data items as either a secure data item or an unsecure data item based on a source from which that data item is obtained, so as to designate which data items of the plurality of data items are shareable;
 comparing labels of the plurality of data items with (i) an identifier of the first user, (ii) an identifier of the second user, and (iii) a plurality of identifiers of the plurality of events;
 bifurcating access to the plurality of data items by the first user via a first user interface and by the second user via a second user interface in accordance with the journey by:
  in response to a determination that a label of a data item indicates that the data item is a secure data item and matches the identifier of the first user but not the identifier of the second user:
   granting, for a first period of time, access to the secure data item on the first user interface but not the second user interface, such that the secure data item is accessible to the first user but not the second user; and
  in response to a determination that a label of a data item indicates that the data item is an unsecure data item and matches the identifier of the first user and the identifier of the second user:
   granting, for a second period of time, access to the unsecure data item on the first user interface and the second user interface, such that the unsecure data item is accessible to the first user and the second user;
  wherein the first and second periods of time correspond to when one of the plurality of events with a matching identifier occurs; and wherein analysis of the plurality of identifiers of the plurality of events in addition to the identifiers of the first and second users allows access to the plurality of data items to be bifurcated in a dynamic manner to reflect progress of the first user along the journey; and prompting a communication exchange between the first and second users by:
  establishing a communication link between a first computing device used by the first user to access the first user interface and a second computing device used by the second user to access the second user interface,
  causing display of messaging control components on the first and second user interfaces, and
  posting, to the second user interface, a suggested topic for initiating or maintaining the communication exchange,
    wherein the suggested topic relates to a given unsecure data item that is presently accessible via the second user interface.

2. The method of claim 1 further comprising:
causing display of the bifurcated data items on a first view of the first user interface on a first handheld mobile device and on a second view of the second user interface on a second handheld mobile device, the first view being different than the second view.

3. The method of claim 1 further comprising, prior to obtaining the plurality of data items associated with the journey:
  identifying an electronic record of the first user based on identifying information captured at a handheld mobile device;
  extracting one or more characteristics of the first user from the electronic record; and
  selecting a program from among a plurality of programs based on the one or more characteristics.

4. The method of claim 3 further comprising:
  identifying the plurality of events based on information of other users that completed the program;
  determining a timeline for the plurality of events based on the information of the other users, the information of the other users including one or more events for the program; and
  scheduling the plurality of events at different points in time in accordance with the timeline.

5. The method of claim 1 further comprising:
causing display of the bifurcated data items on a first view of the first user interface and on a second view of the second user interface, the first view being different than the second view and each presenting a control for exchanging communications between the first user interface and the second user interface.

6. The method of claim 1 further comprising:
extracting a private data item of the first user from a private record stored in a repository of user records.

7. The method of claim 1 further comprising:
receiving a data item as input to the second user interface;
labeling the received data item as either a secure or unsecure data item in response to a designation by the second user; and
causing display of the received data item on a view of the first user interface.

8. The method of claim 1 further comprising:
extracting a content item of the first user from a social media network; and
causing display of the content item on a view of the second user interface.

9. The method of claim 1 further comprising:
receiving a data item as input to the first user interface; and
labeling the received data item as a secure data item based on a login credential input to access the first user interface.

10. The method of claim 1 further comprising:
instantiating a messaging tool on handheld mobile devices of the first user and the second user.

11. The method of claim 1 further comprising:
granting control of the secure data item to the first user.

12. A non-transitory computer-readable storage medium storing instructions, which, when executed by at least one data processor of a system, cause the system to:
  apply, to information associated with a first user with a characteristic, a machine learning model that
    (i) selects a journey for the first user from among multiple journeys, each of which includes a different schedule or structure for staging content, and
    (ii) identifies an appropriate event from among a plurality of events that collectively define the journey,
    wherein the machine learning model is trained based on an aggregate of data items of multiple users with the characteristic, and
    wherein the machine learning model is trained using a Naïve Bayes classifier algorithm, a k-means clustering algorithm, a support vector machine algorithm, or an artificial neural network;
  obtain a plurality of data items associated with the journey;
  label each of the plurality of data items as either a secure data item or an unsecure data item based on a source from which that data item is obtained, so as to designate which of the plurality of data items are shareable;
  compare labels of the plurality of data items with (i) an identifier of the first user, (ii) an identifier of a second user responsible for providing care to the first user, and (iii) a plurality of identifiers of the plurality of events;
  bifurcate access to the plurality of data items by the first user via a first user interface and by the second user via a second user interface in accordance with the journey by:
    in response to a determination that a label of a data item indicates that the data item is a secure data item and matches the identifier of the first user but not the identifier of the second user:
      granting, for a first period of time, access to the secure data item on the first user interface but not the second user interface; and
    in response to a determination that a label of a data item indicates that the data item is an unsecure data item and matches the identifier of the first user and the identifier of the second user:
      granting, for a second period of time, access to the unsecure data item on the first user interface and the second user interface;
    wherein the first and second periods of time correspond to when one of the plurality of events with a matching identifier occurs; and
    wherein analysis of the plurality of identifiers of the plurality of events in addition to the identifiers of the first and second users allows access to the plurality of data items to be bifurcated in a dynamic manner to reflect progress of the first user along the journey;

establish a communications link for prompting a communication exchange between computing devices that present the first user interface and the second user interface; and posting, to the second user interface, a suggested topic for initiating or maintaining the communication exchange, wherein the suggested topic relates to a given unsecure data item that is presently accessible via the second user interface.

13. The non-transitory computer-readable storage medium of claim 12, wherein the system is further caused to:
for each of the plurality of data items, compare a corresponding one of the labels with the identifier of the second user after comparing the corresponding label with the identifier of the first user.

14. A system comprising:
at least one hardware processor; and
at least one non-transitory memory storing instructions, which, when executed by the at least one hardware processor, cause the system to:
apply, to information associated with a first user, a machine learning model that
(i) selects a journey for the first user from among multiple journeys, each of which includes a different schedule or structure for staging content, and
(ii) identifies an appropriate event from among a plurality of events that collectively define the journey,
wherein the machine learning model is trained based on an aggregate of data items of multiple users with a common characteristic, and
wherein the machine learning model is trained using a Naïve Bayes classifier algorithm, a k-means clustering algorithm, a support vector machine algorithm, or an artificial neural network;
obtain a plurality of data items associated with the journey;
label each of the plurality of data items as either a secure data item or an unsecure data item based on a source from which that data item is obtained;
compare labels of the plurality of data items with (i) an identifier of the first user, (ii) an identifier of a second user responsible for providing care to the first user, and (iii) a plurality of identifiers of the plurality of events;
bifurcate access to the plurality of data items by the first user via a first user interface and by the second user via a second user interface in accordance with the journey by:
in response to a determination that a label of a data item indicates that the data item is a secure data item and matches the identifier of the first user but not the identifier of the second user:
granting, for a first period of time, access to the secure data item on the first user interface but not the second user interface; and
in response to a determination that a label of a data item indicates that the data item is an unsecure data item and matches the identifier of the first user and the identifier of the second user:
granting, for a second period of time, access to the unsecure data item on the first user interface and the second user interface,
wherein the first and second periods of time correspond to when one of the plurality of events with a matching identifier occurs, and wherein analysis of the plurality of identifiers of the plurality of events in addition to the identifiers of the first and second users allows access to the plurality of data items to be bifurcated in a dynamic manner to reflect progress of the first user along the journey, establish a communications link for prompting a communication exchange between computing devices that present the first user interface and the second user interface, and posting, to the second user interface, a suggested topic for initiating or maintaining the communication exchange, wherein the suggested topic relates to a given unsecure data item that is presently accessible via the second user interface.

15. The system of claim 14 further caused to:
cause display of selectable options to schedule an event of the plurality of events via the second interface.

16. The system of claim 14 further caused to:
cause display of a messaging control component on the first user interface and a counterpart messaging control component on the second user interface, the second user interface further including a suggested communication related to a matching event.

17. A method for dynamically managing communications between a patient that is known to have a disease and a caregiver that is responsible for assisting the patient in managing the disease, the method comprising:
obtaining a plurality of data items that are associated with the patient;
labeling each of the plurality of data items based on an analysis of (i) a source from which that data item is obtained, (ii) an indication of sensitivity of that data item that is provided by the patient, or (iii) content of that data item, such that each of the plurality of data items is designated as either a secure data item or an unsecure data item;
applying, to patient-generated content, a machine learning model that
selects a journey for the patient from among multiple journeys, each of which includes a different schedule or structure for presenting information, and
identifies an appropriate event from among a plurality of events that collectively define the journey,
wherein the machine learning model is trained based on an aggregate of data items that are associated with a population of patients known to have the disease;
bifurcating access to the plurality of data items by the patient through a first interface and by the caregiver through a second interface by:
comparing labels of the plurality of data items with (i) an identifier associated with the patient, (ii) an identifier associated with the caregiver, and (iii) a plurality of identifiers associated with the plurality of events,
in response to a determination that a label of a given data item (i) indicates that the given data item is a secure data item, (ii) matches the identifier associated with the patient, and (iii) matches a first one of the plurality of identifiers that corresponds to a first one of the plurality of events,
granting, for a first period of time, access to the secure data item through the first interface but not the second interface, and
in response to a determination that a label of a given data item (i) indicates that the given data item is an unsecure data item, (ii) matches the identifier associated with the patient or the identifier associated with the caregiver, and (iii) matches a second one of the plurality of identifiers that corresponds to a second one of the plurality of events,
  granting, for a second period of time, access to the unsecure data item through the first and second interfaces,
wherein the first and second periods of time correspond to when the first and second events with matching identifiers occur, and
wherein analysis of identifiers of the plurality of events in addition to the identifiers of the patient and caregiver allows access to the plurality of data items to be bifurcated in a dynamic manner to reflect progress by the patient in a program for managing the disease; and
causing progression of the patient along the journey by either:
  prompting the patient to perform an action via the first interface or the caregiver to perform an action via the second interface, or
  prompting a communication exchange between the patient and the caregiver via the first and second interfaces by (a) establishing a communication link between a first computing device used by the patient to access the first interface and a second computing device used by the caregiver to access the second interface and (b) posting, to the second interface, a suggested topic for initiating or maintaining the communication exchange, wherein the suggested topic relates to a given unsecure data item that is presently accessible via the second interface.

18. The method of claim 17, wherein the event is part of the program, such that access to secure data items and unsecure data items is bifurcated in a dynamic manner to reflect a current state of progress within the program.

19. The method of claim 17, further comprising:
  defining the population of patients based on a discovery, learned through an analysis of stored characteristics, that the patients have the disease; and
  applying a machine learning algorithm to the aggregate of data items that are associated with the population of patients known to have the disease, so as to produce the machine learning model as output.

* * * * *